United States Patent
Ingman et al.

(10) Patent No.: US 9,566,431 B2
(45) Date of Patent: Feb. 14, 2017

(54) METHOD OF FORMING A LARGE NUMBER OF METAL-ION-DEPOSITION ISLANDS ON THE SCALP BY A RAPID SERIES OF BRIEF ELECTRODE-CONTACT EVENTS

(71) Applicant: PILOGICS L.P., Haifa (IL)

(72) Inventors: Dov Ingman, Haifa (IL); Erez Manor, Herzlia (IL)

(73) Assignee: PILOGICS L.P., Haifa (IL)

( * ) Notice: Subject to any disclaimer, the term of this patent is extended or adjusted under 35 U.S.C. 154(b) by 161 days.

(21) Appl. No.: 14/246,944

(22) Filed: Apr. 7, 2014

(65) Prior Publication Data
US 2015/0283377 A1 Oct. 8, 2015

(51) Int. Cl.
| | |
|---|---|
| *A61N 1/32* | (2006.01) |
| *A61N 1/04* | (2006.01) |
| *A61N 1/20* | (2006.01) |
| *A61N 1/05* | (2006.01) |

(52) U.S. Cl.
CPC ............. *A61N 1/322* (2013.01); *A61N 1/0464* (2013.01); *A61N 1/0476* (2013.01); *A61N 1/205* (2013.01); *A61N 1/325* (2013.01); *A61N 1/326* (2013.01); *A61N 1/0502* (2013.01)

(58) Field of Classification Search
CPC .......... A61N 1/205; A61N 1/325; A61N 1/30; A61N 1/0408
See application file for complete search history.

(56) References Cited

U.S. PATENT DOCUMENTS

| | | | |
|---|---|---|---|
| 5,961,483 A | 10/1999 | Sage et al. | |
| 5,975,090 A * | 11/1999 | Taylor ................. | A01K 13/002 132/116 |
| 6,834,206 B1 | 12/2004 | Pitzen et al. | |
| D500,854 S | 1/2005 | Eichel | |

(Continued)

FOREIGN PATENT DOCUMENTS

| | | |
|---|---|---|
| CN | 2901984 Y | 5/2007 |
| CN | 2019996809 U | 10/2011 |

(Continued)

OTHER PUBLICATIONS

CN201996809 Machine Translation (by EPO and Google)—published Oct. 5, 2011—Xiusheng et al.

(Continued)

*Primary Examiner* — Christopher D Koharski
*Assistant Examiner* — Natasha Patel
(74) *Attorney, Agent, or Firm* — Marc Van Dyke; Fourth Dimension IP

(57) ABSTRACT

A method of treating or preventing a hair-condition of a user comprising: subjecting the user's scalp to at least 200 distinct electrode-scalp contact events during a time-interval of at most one minute and dividable into 5 non-overlapping equal-duration sub-intervals covering the time-interval, method performed such that i. for at least a majority of the electrode-scalp contact events, no electrode of the event enters into the dermis; ii. a duration of each electrode contact event is at most 100 milliseconds; and iii. for each electrode contact event, an electrical current flows between the electrode and the scalp so as to deposit electrode-released ions of a first metal or of a second metal on the scalp, thereby forming a respective metal-ion-deposition island on the user's scalp.

25 Claims, 17 Drawing Sheets

(56) References Cited

U.S. PATENT DOCUMENTS

| | | | |
|---|---|---|---|
| 7,194,316 B2 | 3/2007 | Bousfield et al. | |
| D568,473 S | 5/2008 | Ashiwa et al. | |
| 7,597,692 B2 * | 10/2009 | Weaver | A61M 5/427 604/22 |
| D645,204 S | 9/2011 | Platek | |
| 8,048,019 B2 | 11/2011 | Nisato et al. | |
| D664,295 S | 7/2012 | Grabes et al. | |
| D665,128 S | 8/2012 | Kling et al. | |
| D678,614 S | 3/2013 | Yiu | |
| D678,783 S | 3/2013 | Wilcox et al. | |
| D686,370 S | 7/2013 | Yiu | |
| D696,778 S | 12/2013 | Liao et al. | |
| D719,651 S | 12/2014 | Hoffmann et al. | |
| D724,726 S | 3/2015 | Prokop | |
| 2004/0006374 A1 | 1/2004 | Mondin | |
| 2004/0147984 A1 | 7/2004 | Altshuler et al. | |
| 2004/0267169 A1 | 12/2004 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 * | 1/2005 | Sun | A61K 8/19 604/501 |
| 2006/0084894 A1 | 4/2006 | Anderson | |
| 2006/0253079 A1 | 11/2006 | McDonough et al. | |
| 2007/0049901 A1 | 3/2007 | Wu et al. | |
| 2007/0060862 A1 | 3/2007 | Sun et al. | |
| 2007/0073217 A1 | 3/2007 | James | |
| 2008/0058783 A1 | 3/2008 | Altshuler et al. | |
| 2008/0161746 A1 | 7/2008 | Visco et al. | |
| 2009/0005801 A1 | 1/2009 | Eastman | |
| 2009/0069740 A1 | 3/2009 | Visco et al. | |
| 2009/0118698 A1 | 5/2009 | Liebl | |
| 2009/0254076 A1 | 10/2009 | Altshuler et al. | |
| 2010/0036295 A1 | 2/2010 | Altshuler et al. | |
| 2010/0262081 A1 | 10/2010 | Lee et al. | |
| 2010/0286673 A1 | 11/2010 | Altshuler et al. | |
| 2011/0009782 A1 | 1/2011 | Pampalone et al. | |
| 2011/0040236 A1 | 2/2011 | Isaacs et al. | |
| 2011/0118655 A1 * | 5/2011 | Fassih | A61N 1/044 604/20 |
| 2011/0172745 A1 | 7/2011 | Na et al. | |
| 2011/0218464 A1 | 9/2011 | Iger | |
| 2012/0184894 A1 * | 7/2012 | Imran | A61K 9/0009 604/20 |
| 2013/0013028 A1 | 1/2013 | Kriksunov et al. | |
| 2014/0005644 A1 | 1/2014 | Karni et al. | |
| 2014/0005658 A1 | 1/2014 | Rosenbegr | |
| 2014/0025062 A1 | 1/2014 | Rosenberg et al. | |
| 2014/0121730 A1 | 5/2014 | Kalev et al. | |
| 2014/0214022 A1 | 7/2014 | Adanny et al. | |
| 2014/0228834 A1 | 8/2014 | Adanny et al. | |
| 2014/0249522 A1 | 9/2014 | Adanny et al. | |
| 2014/0276370 A1 | 9/2014 | Iger | |
| 2014/0296852 A1 | 10/2014 | Adanny et al. | |
| 2014/0303546 A1 | 10/2014 | Badiavas et al. | |
| 2014/0324035 A1 | 10/2014 | Iger et al. | |
| 2014/0330196 A1 | 11/2014 | Ingman et al. | |
| 2015/0038965 A1 | 2/2015 | Iger | |
| 2015/0073402 A1 | 3/2015 | Iger | |
| 2015/0157388 A1 | 6/2015 | Mehta et al. | |
| 2015/0202007 A1 | 7/2015 | Manstein et al. | |
| 2015/0283377 A1 | 10/2015 | Ingman et al. | |
| 2015/0297283 A1 | 10/2015 | Adanny et al. | |
| 2015/0306419 A1 | 10/2015 | Domankevitz | |
| 2015/0351825 A1 | 12/2015 | Adanny et al. | |
| 2016/0001073 A1 | 1/2016 | Ingman et al. | |
| 2016/0038591 A1 | 2/2016 | Wu et al. | |
| 2016/0045409 A1 | 2/2016 | Ingman et al. | |

FOREIGN PATENT DOCUMENTS

| | | |
|---|---|---|
| DE | 202007003523 U | 8/2007 |
| DE | 102007011368 A1 | 9/2008 |
| DE | 102007011363 A1 | 11/2008 |
| EP | 0788810 A2 | 8/1997 |
| JP | 2739091 B | 4/1995 |
| JP | 2000140131 A | 5/2000 |
| JP | 2004215950 A | 8/2004 |
| JP | 2011045610 A | 3/2011 |
| JP | 2012075543 A | 4/2012 |
| JP | 2013158363 A | 8/2013 |
| KR | 20080100569 A | 11/2008 |
| RU | 2003123515 A | 11/2004 |
| WO | WO9300959 A1 | 1/1993 |
| WO | WO0113988 A1 | 3/2001 |
| WO | WO2006056055 A2 | 6/2006 |
| WO | WO2007088348 A2 | 8/2007 |
| WO | WO2008004818 A1 | 1/2008 |
| WO | WO2013084189 A2 | 6/2013 |

OTHER PUBLICATIONS

CN2901984 Machine Translation (by EPO and Google)—published May 23, 2007—Kenji et al.
JP2000140131 Machine Translation (by EPO and Google)—published May 23, 2000—Kamiya et al.
JP2012075543 Machine Translation (by EPO and Google)—published Apr. 19, 2012—Kyushu Hitachi.
JP2013158363 Machine Translation (by EPO and Google)—published Aug. 19, 2013—Dainippon Print.
JP2739091B Machine Translation (by EPO and Google)—published Apr. 11, 1995—Japan Fitness KK.
RU2003123515 Machine Translation (by EPO and Google)—published Nov. 27, 2004—Salimov M KH.
JP2011045610 Machine Translation (by EPO and Google)—published Mar. 10, 2011—Techno Link Co Ltd.
JP2004215950 Machine Translation (by EPO and Google)—published Aug. 5, 2004—Takigawa KK.
DE202007003523U Machine Translation (by EPO and Google)—published Aug. 23, 2007—Safetec GMBH.
JP2000140131 Machine Translation (by EPO and Google)—published May 23, 2000—Hoomaa Ion Kenkyusho KK.
DE102007011363 Machine Translation (by EPO and Google)—published Nov. 6, 2008—Safetec GMBH.
DE102007011368 Machine Translation (by EPO and Google)—published Sep. 11, 2008—Safetec GMBH.
International Search Report for PCT/IB2012/057041 published as WO 2013/084189.
Written Opinion for PCT/IB2012/057041 published as WO 2013/084189.
Machine Translation of KR20080100569 by Kipris—published.

* cited by examiner

FIG. 6

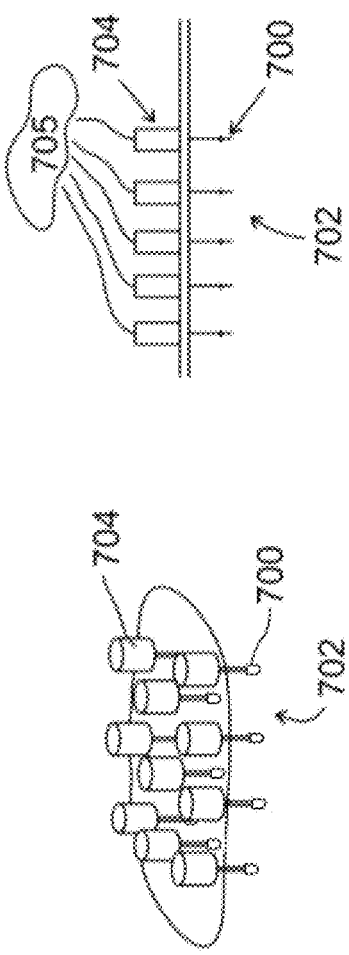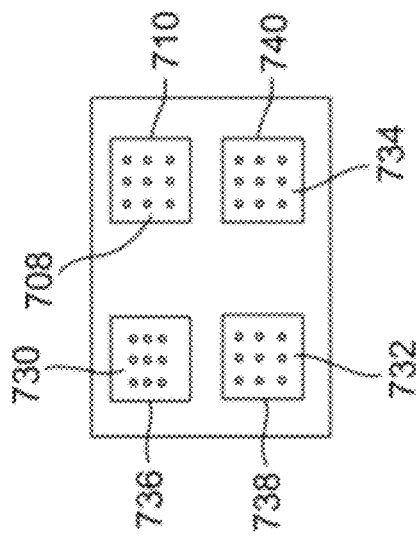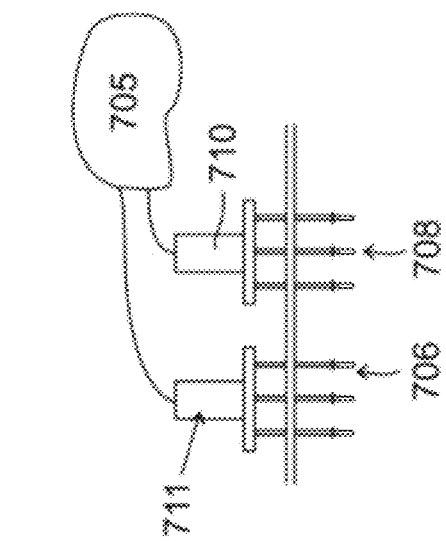
FIG. 11A  FIG. 11B  FIG. 11C  FIG. 11D

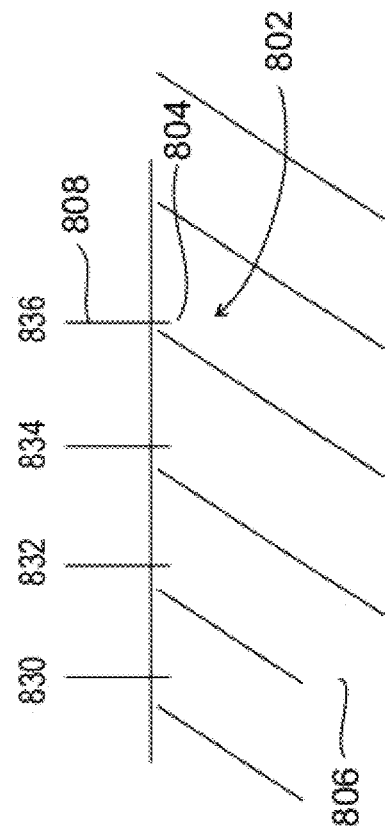
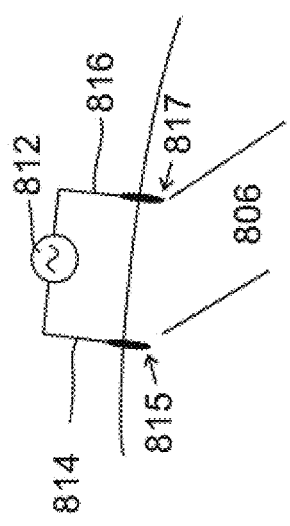
FIG. 12A
FIG. 12B

| case # | Initial Hair Count per cm2 | Final Hair Count per cm2 | Initial Terminal Hair Count per cm2 | Final Terminal Hair Count per cm2 | Treatment Period in days | Hair Count Change | Terminal Hair Count Change | Hair Count % Change | Terminal Hair Count % Change | age |
|---|---|---|---|---|---|---|---|---|---|---|
| 1 | 143 | 165 | 64 | 142 | 189 | 22 | 78 | 15 | 123 | 54 |
| 2 | 65 | 124 | 49 | 101 | 143 | 59 | 52 | 91 | 105 | 54 |
| 3 | 96 | 162 | 74 | 121 | 109 | 66 | 48 | 69 | 65 | 37 |
| 4A | 140 | 218 | 90 | 114 | 193 | 78 | 24 | 56 | 27 | 26 |
| 4B | 129 | 172 | 96 | 118 | 193 | 43 | 21 | 33 | 22 | 26 |
| 5 | 43 | 121 | 39 | 92 | 133 | 78 | 53 | 184 | 137 | 24 |
| 6 | 213 | 259 | 160 | 210 | 140 | 46 | 50 | 21 | 31 | 22 |
| 7 | 228 | 241 | 167 | 185 | 133 | 13 | 18 | 6 | 11 | 23 |
| 8 | 187 | 206 | 113 | 118 | 140 | 20 | 5 | 11 | 4 | 38 |
| 9 | 131 | 140 | 80 | 96 | 161 | 10 | 15 | 8 | 19 | 42 |
| 10 | 176 | 211 | 134 | 134 | 140 | 35 | -1 | 20 | -1 | 43 |
| 11 | 139 | 156 | 81 | 86 | 165 | 17 | 5 | 13 | 6 | 23 |
| 12 | 122 | 197 | 99 | 133 | 117 | 74 | 33 | 61 | 34 | 58 |
| 13A | 178 | 219 | 115 | 116 | 196 | 41 | 1 | 23 | 1 | 55 |
| 13B | 162 | 219 | 90 | 111 | 196 | 57 | 21 | 36 | 24 | 55 |
| 14 | 109 | 117 | 81 | 89 | 126 | 8 | 8 | 7 | 9 | 26 |
| 15 | 162 | 197 | 112 | 136 | 105 | 35 | 24 | 21 | 22 | 47 |
| 16 | 179 | 181 | 93 | 122 | 116 | 3 | 29 | 1 | 31 | 39 |
| 17 | 130 | 164 | 71 | 134 | 105 | 34 | 62 | 26 | 87 | 30 |
| 18 | 140 | 235 | 54 | 131 | 112 | 94 | 77 | 67 | 142 | 26 |

FIG. 13A

| case # | Initial Hair Count per cm2 | Final Hair Count per cm2 | Initial Terminal Hair Count per cm2 | Final Terminal Hair Count per cm2 | Treatment Period in days | Hair Count Change | Terminal Hair Count Change | Hair Count % Change | Terminal Hair Count % Change | age |
|---|---|---|---|---|---|---|---|---|---|---|
| 19 | 169 | 187 | 140 | 155 | 91 | 19 | 15 | 11 | 11 | 24 |
| 20 A | 138 | 177 | 93 | 103 | 70 | 39 | 11 | 28 | 11 | 54 |
| 20 B | 94 | 128 | 69 | 79 | 70 | 33 | 10 | 35 | 14 | 54 |
| 21 | 137 | 172 | 108 | 135 | 77 | 34 | 27 | 25 | 25 | 46 |
| 22 | 170 | 201 | 127 | 145 | 135 | 31 | 18 | 18 | 14 | 32 |
| 23 | 171 | 203 | 127 | 156 | 126 | 33 | 29 | 19 | 23 | 46 |
| 24 A | 140 | 147 | 86 | 86 | 126 | 8 | 0 | 5 | 0 | 59 |
| 24B | 155 | 198 | 106 | 126 | 126 | 43 | 20 | 28 | 19 | 59 |
| 24C | 131 | 188 | 84 | 118 | 132 | 58 | 34 | 44 | 41 | 59 |
| 25A | 72 | 87 | 52 | 64 | 132 | 15 | 12 | 21 | 23 | 59 |
| 25B | 60 | 71 | 45 | 52 | 132 | 11 | 8 | 18 | 17 | 59 |
| 25C | 15 | 43 | 12 | 28 | 63 | 27 | 16 | 180 | 132 | 59 |
| 26A | 217 | 244 | 115 | 194 | 63 | 27 | 78 | 12 | 68 | 44 |
| 26B | 231 | 228 | 108 | 129 | | -3 | 21 | -1 | 20 | 44 |

FIG. 13B

METHOD OF FORMING A LARGE NUMBER OF METAL-ION-DEPOSITION ISLANDS ON THE SCALP BY A RAPID SERIES OF BRIEF ELECTRODE-CONTACT EVENTS

FIELD AND BACKGROUND OF THE INVENTION

The present invention, in some embodiments thereof, relates to a device and method for stimulating skin and, more particularly, but not exclusively, to a device and method for directly stimulating the skin below the surface of the scalp to promote hair growth.

SUMMARY

Embodiments of the invention relate to a device and method whereby the scalp is rapidly and repeatedly touched by ion-releasing electrodes. During each 'ion-depositing electrode-scalp contact event' an electrode (e.g. through which externally generated electrical current flows) is very briefly brought into and out of contact with the scalp—e.g. in contact with the scalp for at most 100 milliseconds. During each brief contact event, the electrode is briefly brought into and out of contact with the scalp so as to deposit metal on the scalp to form a small (e.g. at most 15 mm2 in area) metal-deposition island on the scalp. In some embodiments, each brief contact event is effective to apply a significant amount of highly-localized pressure, e.g. at least 0.5 megapascals [MPa] localized over a contact area of at least 0.1 mm2 and at most 10 mm2. The rapid application of non-wounding but significant pressure subjects the scalp to a 'micromassage.'

The method is performed so that: (i) a large number of such electrode-events are sequentially performed within a relatively short period of time; (ii) at least two types of metal-deposition islands are formed on the scalp (e.g. a first type comprising zinc and a second type comprising copper); and (iii) both types of metal-deposition islands are distributed over a significant portion of the scalp. As discussed below, it is possible to quantify the extent of distribution of metal-islands on the scalp and the proximity of first and second types of metal islands (e.g. 'cathode-islands' and 'anode-islands'), in terms of 'scalp patches.'

Not wishing to be bound by theory, it is believed that the deposition of a relatively large number of very small but distinct metal-ion-deposition-islands on the user's scalp forms a significant number of 'micro-battery-cell' on the user's scalp when both cation islands and anion islands are distributed over a region of the scalp. It is believed that after deposition of the islands, small electrical currents may be sustained between the distinct deposition islands (e.g. due to proximity of distinct cathode-islands and anode-islands) along the user's scalp for some period of time (e.g. at least hours). It is believed that the combination of the time-sustained electrical stimulation together with the mild trauma of the micro-massage obviates the need to employ wounding-based techniques to stimulate the scalp.

Although skin-wounding stimulates cell-growth in the skin (and possibly hair-growth) by inducing a biological 'wound-healing' process, certain users may consider wounding devices as invasive and unpleasant to use. It is believed that the presently-disclosed ion-delivering micro-massage obviates the need for a more severe treatment regimen based on wounding, while still combating baldness.

When metallic-ions are 'released from' an electrode this is in contrast with pre-applying an ion-containing topical agent (e.g. an ion-containing liquid or cream or gel) to the skin and then using an electrode to drive the ions into the skin. When metallic-ions are 'released from', the source of the metallic ions is from the electrode itself. The released metal-ions are provided from an interior of the electrode (e.g. from a reservoir disposed within the electrode) or from actual material of the electrode (i.e. the electrode is at least partially constructed from the metal which is then released) or from an 'integrally-formed' coating on the electrode—i.e. the electrode is pre-coated with the metal so that the metal coating is integrally formed with the electrode and then metal of this coating is released.

By 'releasing' metallic ions from the electrode rather than relying on a topically-applied ion-containing flowable-fluid (e.g. liquid, cream, gel), it is possible to deliver distinct ion-deposition metal-ion deposition islands. After treatment, small electrical currents may flow between these metal-deposition islands to electrically stimulate the skin after the electrode-contacting events have ceased, thereby providing a sustained effect.

A number of techniques are disclosed herein for rapidly bringing electrode into and out of contact with the scalp. In one example, a plurality of electrode-protrusions (e.g. having a rounded tip) are disposed around a roller. As the roller is rolled over the surface of the skin, the electrodes are briefly brought into contact with and out of contact with the skin so that a large number of very brief electrode contact events are performed. A second example relates to a motorized device. In this second example, electrodes (e.g. having a rounded tip) are rapidly, reciprocally and vertically brought into contact and out of contact with the scalp.

Despite the very-brief contact periods (i.e. less than 0.1 seconds or even less) between each electrode and the scalp, a therapeutically effective amount of metallic-ions may be deposited in each treatment island. Towards this end, an external electrical power source may boost a rate of ion-delivery to each treatment island, instead of relying only on a galvanic potential between electrodes of different polarity. Not wishing to be bound by theory, externally-driving ion deposition on the scalp may, once again, obviate the need for a more mechanically-aggressive wounding-based treatment where most electrode-contact events lead to penetrating of the dermis.

It is now disclosed a method of treating or preventing a hair-condition of a user, the user's scalp dividable into a scalp-patch-set of n millimeter (mm)×n millimeter (mm) non-overlapping scalp patches, where n a positive number having a value of at most 5. The method comprises subjecting the user's scalp to at least q distinct electrode-scalp contact events within a time-interval of at most one minute and dividable into m non-overlapping equal-duration sub-intervals covering the time-interval, m begin a positive integer having a value of at least 5, q being a positive integer having a value of at least 200. For the non-limiting example where m is 5, the m equal-duration sub-intervals are [0, 12 seconds], [12 seconds, 24 seconds], [24 seconds, 36 seconds], [36 seconds, 48 seconds], and [48 seconds, 60 seconds]. Since every moment within the one-minute time interval i within one of the sub-intervals, the sub-intervals may be said to collectively 'cover an entirety of the time-interval.

In some embodiments, for at least a majority of the electrode-scalp contact events, no electrode of the event enters into the dermis;

In some embodiments, a duration of each electrode scalp contact event is at most 100 milliseconds—i.e. for each electrode-scalp no more than 100 milliseconds elapses between (i) a time when the electrode is brought into contact with the scalp; and (ii) a time when the electrode is taken out of contact with the scalp.

In some embodiments, an electrode-scalp contact area for each electrode-scalp contact event is at most 10 mm$^2$.

In some embodiments, for each electrode contact event, an electrical current flows between the electrode and the scalp so as to deposit electrode-released ions of a first metal or of a second metal on the scalp, thereby forming a respective metal-ion-deposition island on the user's scalp. Thus, each contact event deposits either a first metal (e.g. zinc) and a second metal (e.g. copper) but not both—other metals other than the first and second metal may additionally be deposited along with the first or the second metal.

In some embodiments, for each of the non-overlapping equal-duration sub-intervals, at least p electrode-scalp contact events occur, p being a positive integer having a value of at least 1.

In some embodiments, at least 5% of the events are first-metal-depositing and at least 5% of the events are second-metal-depositing.

In some embodiments, at least one first-metal-deposition-island and at least one second-metal-deposition-island are both respectively and distinctly formed on each n mm×n mm scalp-patch selected from a 10-member scalp-patch sub-set of the scalp-patch set.

In some embodiments, the islands may be 'distinct' from each other for some the islands may form a 'bridge' between the formerly-'distinct' islands. This does not detract from the fact that for at least some period of time, the islands were 'distinct' from each other.

In some embodiments, during at least some of the electrode-scalp contact events, externally-generated electrical current (i.e. as opposed to galvanic current) is forced between the electrode and the scalp (for example, between two different electrodes that are simultaneously in contact with the scalp where due to an externally-maintained electric potential difference between the electrodes, electrical current flows therebetween via the scalp) so as to deposit or increase a deposition-rate of electrode-released ions of the first or second metal onto the scalp. Some galvanic current may be present, but the externally-generated electrical current may boost a rate of metal-ion-deposition.

BRIEF DESCRIPTION OF THE DRAWINGS

Some embodiments of the invention are herein described, by way of example only, with reference to the accompanying drawings and/or images. With specific reference now to the drawings and/or images in detail, it is stressed that the particulars shown are by way of example and for purposes of illustrative discussion of embodiments of the invention. In this regard, the description taken with the drawings and/or images makes apparent to those skilled in the art how embodiments of the invention may be practiced.

In the drawings:

FIGS. 6 and 9 illustrate patterns of metal-ion-deposition on the scalp.

In particular.

FIGS. 11A-11I are illustrations of embodiments of electrode actuators

FIGS. 12A-12D illustrate deposition of ions during treatment.

FIGS. 13A-13B describe some experimental results.

DESCRIPTION OF SPECIFIC EMBODIMENTS OF THE INVENTION

Some embodiments of the present invention relate to methods and apparatus that were disclosed in PCT/IB2012/057041 which (i) was filed on Dec. 12, 2012; (ii) was published on Jun. 13, 2013 as WO/2013/084189; and (iii) is incorporated herein by reference in its entirety. In some embodiments, any feature or combination of features described in the present document may be combined with any feature of combination of features described in application PCT/IB2012/057041.

Figure 1:
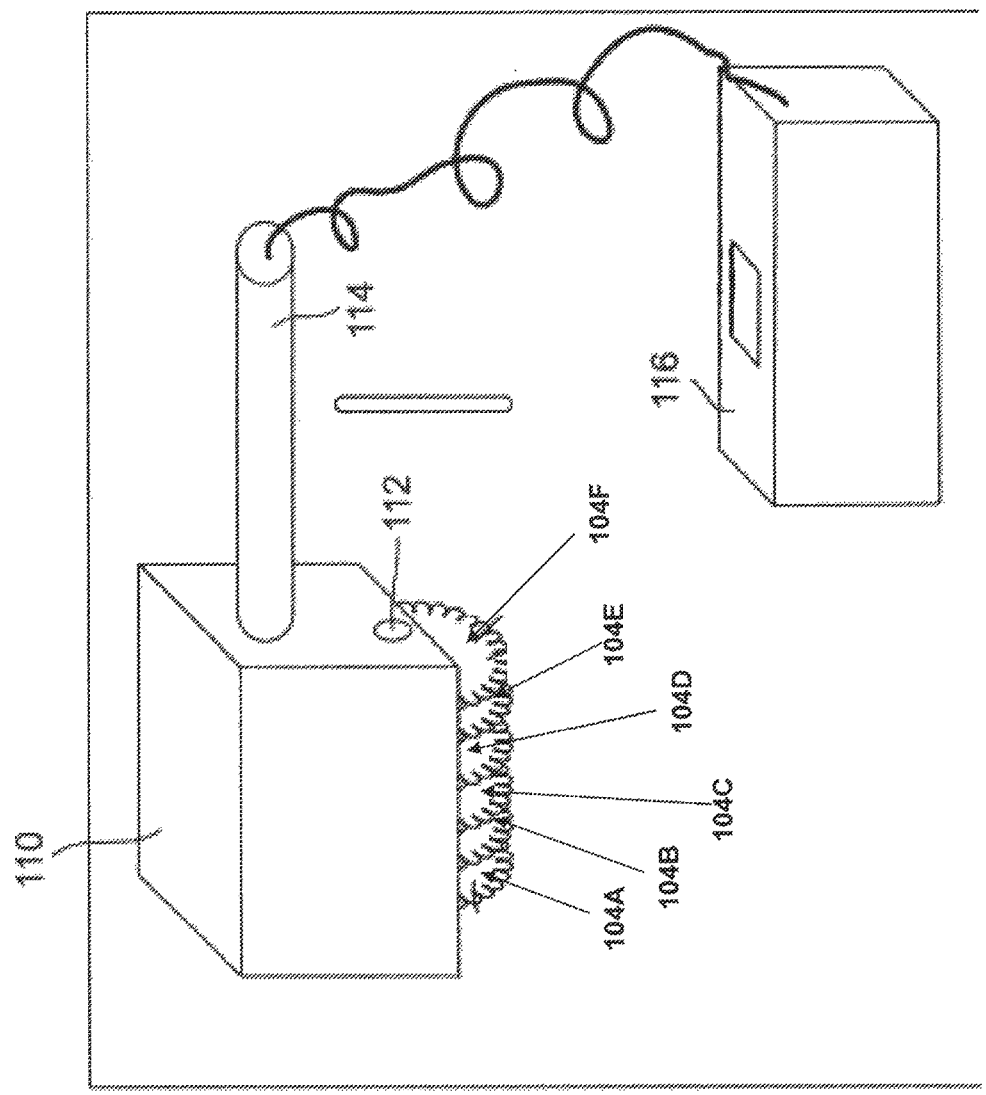
FIGS. 1-5 relate to a device or portion(s) thereof for depositing metal ions on the scalp, for example, to treat a hair-condition such as baldness.
Figure 2:
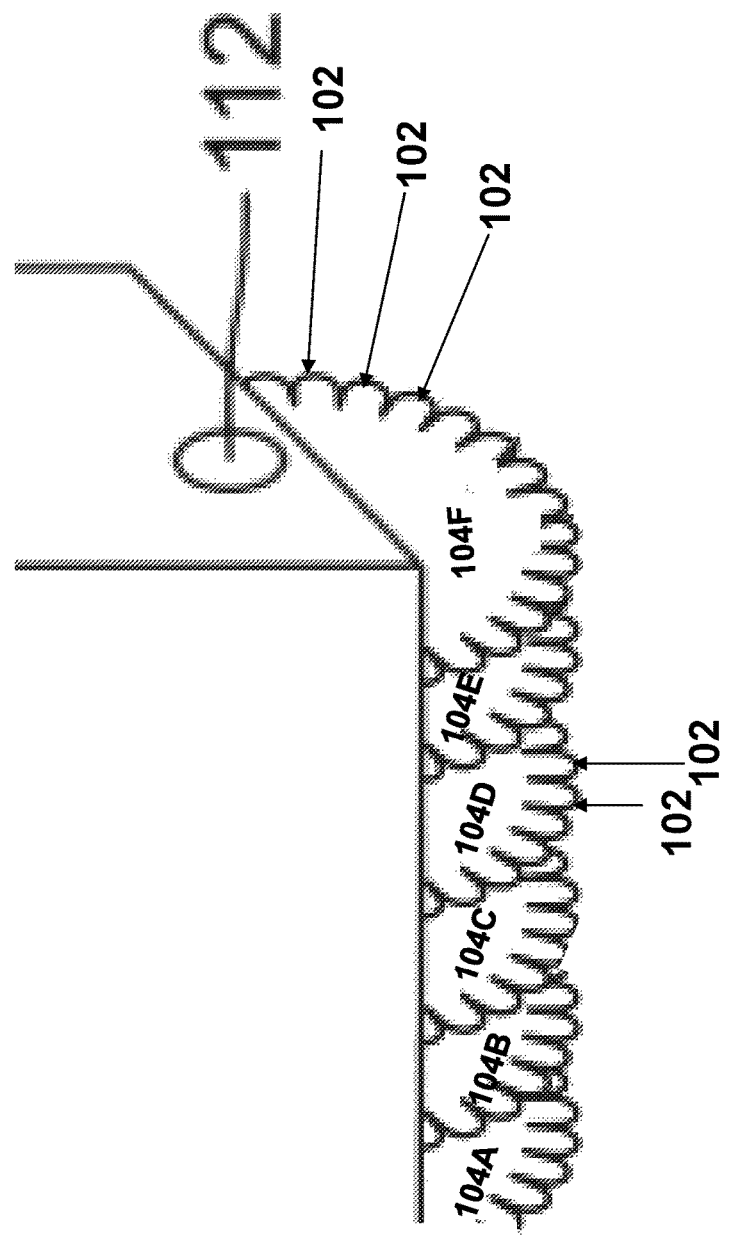

FIG. 1 is an illustration of an exemplary device 100 for promoting hair growth, in accordance with an exemplary embodiment of the invention. FIG. 2 is a close-up of a portion of the device of FIG. 1. As illustrated in FIGS. 1-2, electrodes 102 are arranged along the circumference of at least one disc 104, for example, 2, 4, 6, 8, or other smaller, intermediate or larger numbers of discs 104 are used. In FIG. 1, six discs labeled as 104A-104F, are illustrated. The diameter of discs 104 is, for example, about 2 cm, about 4 cm, about 6 cm, or other smaller, intermediate or larger diameters are used. The thickness of discs and/or electrodes is, for example, about 0.05 mm, about 0.1 mm, about 0.15 mm, or other smaller, intermediate or larger thickness are used.

In an exemplary embodiment of the invention, electrodes 102 and/or discs 104 are arranged to allow existing hair on the scalp to be displaced (e.g., brushed) away from the electrodes during use. Optionally, discs 104 are arranged parallel to one another, to allow hair to be brushed between the discs. Discs 104 are located about 1 mm apart, 3 mm apart, about 5 mm apart, or other smaller, intermediate or larger distances are used.

In an exemplary embodiment of the invention, electrodes 102 are coated by at least one metal. Alternatively, electrodes 102 are made from the metal.

In one non-limiting example related to FIGS. 1-2, a first set of discs (e.g. discs 104A, 104C, and 104E) are coated with a cation (e.g. copper) while a second set of discs (e.g. 104B, 104D and 104F) are coated with an anion (e.g. zinc). In this situation, (i) metal deposition ions comprising the cation are formed contact of electrodes by discs of the first set and (ii) metal deposition ions comprising the anion are formed contact of electrodes by discs of the second set.

As will be discussed below, the alternating cation/anion disc pattern described in the previous paragraph may be useful for ensuring that, after treatment, metal-ion-deposition islands comprising the cation are relatively proximate on the scalp to metal-ion-deposition islands comprising the anion. This may be useful for depositing miniature half-batteries on the user's scalp so that small currents between the deposition islands are sustained after treatment.

For the present disclosure, when a 'metal-ion-deposition' island is formed there is a localized region of scalp wherein for at least one metal, the ion is deposited within the 'deposition island'

Figure 3:
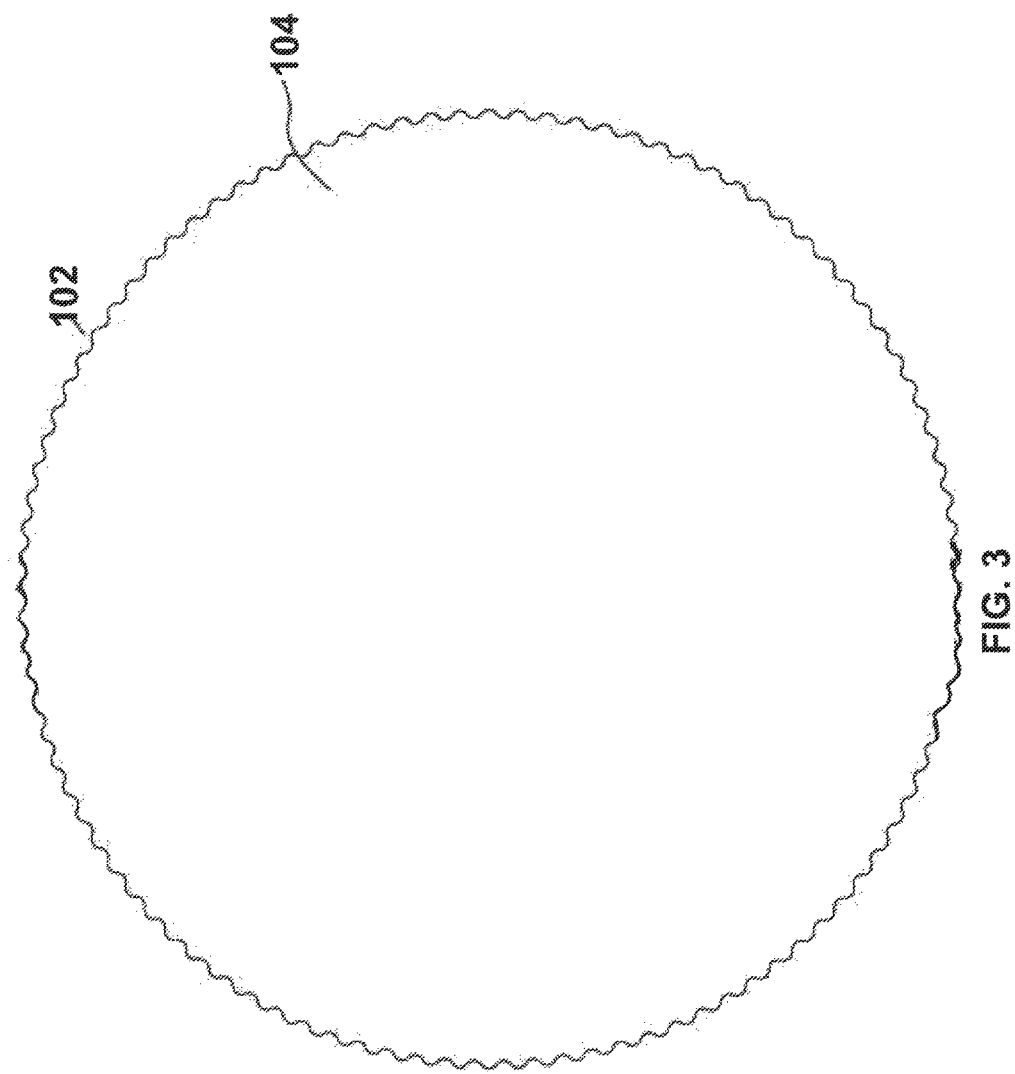

FIG. 3 illustrates an exemplary disc including a plurality of distinct protruding electrodes 102 disposed uniformly around the disc 104. The 'uniform distribution feature' is not intended as a limitation.

Figure 4:
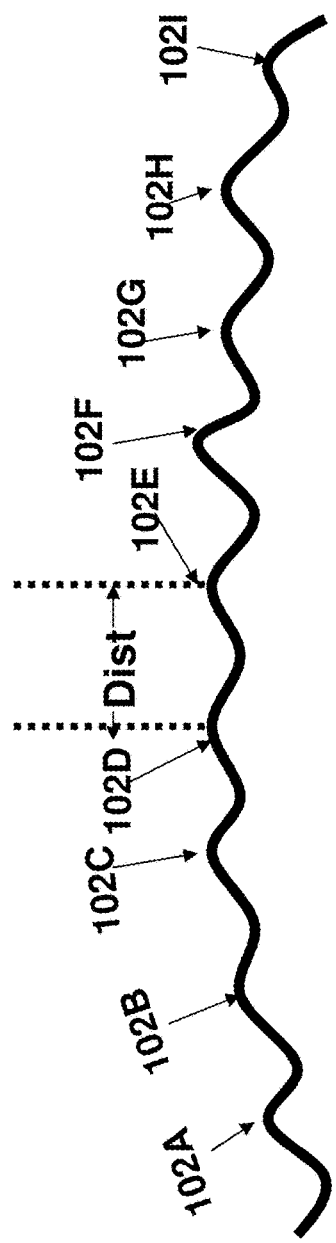
Figure 5:
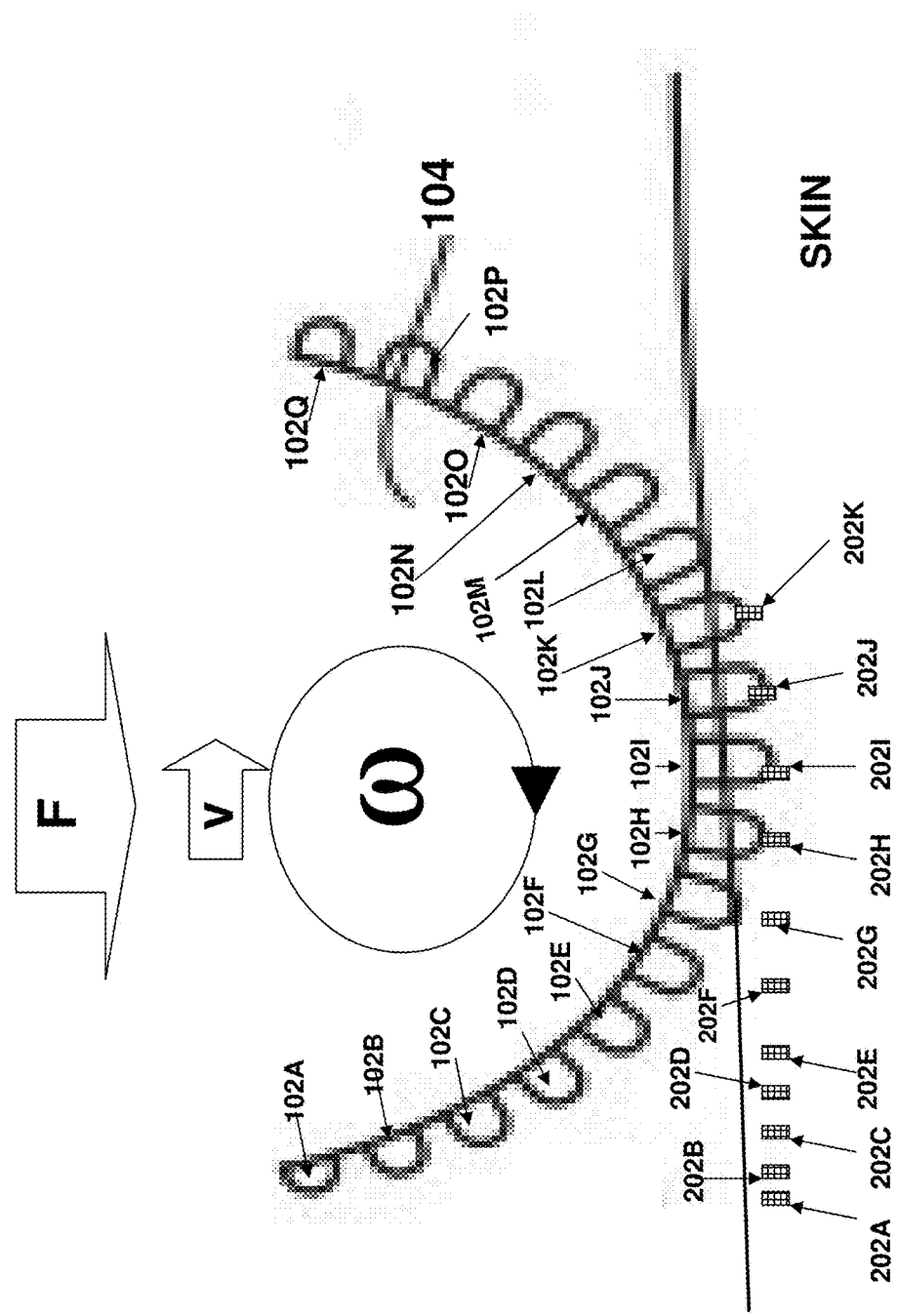

FIG. 4 is a close-up illustration of 10 electrodes 102A-102D of a disc illustrating an inter-electrode distance Dist. FIG. 5 illustrates application of a plurality of distinct metal-ion-deposition ions on the surface of the scalp (i.e. the skin thereof) by rolling, without slipping, a disc over the surface of the scalp. In the non-limiting example of FIG. 5, a center of mass of the roller moves linearly and horizontally from left-to-right (i.e. defining a direction of disc velocity v) as a result of counterclockwise rotation. A downward force F is applied in a direction normal to the scalp, or a local surface thereof. As will be discussed below, in some embodiments, when the downward force is localized along a contact-area of each the electrode, a pressure of at least 0.5 mega-Pascals per electrode may be applied to the scalp.

In the example of FIG. 5, whenever an electrode is brought into contact with the skin, the electrode releases metal ions (i.e. either from an interior of the electrode or from a metal-coating that is integrally formed with the electrode). In the example of FIG. 5, electrodes 102A-102K respectively form metal deposition islands 202A-202K. As illustrated in FIG. 5, in a direction parallel to vector v (representing a direction of linear velocity of the roller), these metal deposition ions are separated on the scalp by a distance that is comparable to the inter-electrode distance illustrated in FIG. 2.

As noted above, in some embodiments, alternating discs are zinc-electrodes and alternating discs are copper-electrodes. According to this non-limiting example, all electrodes 102 of discs 104A, 104C, and 104E deposit a cation (e.g. zinc) and all electrodes 102 of discs 104B, 104D and 104E deposit an anion.

Figure 6:
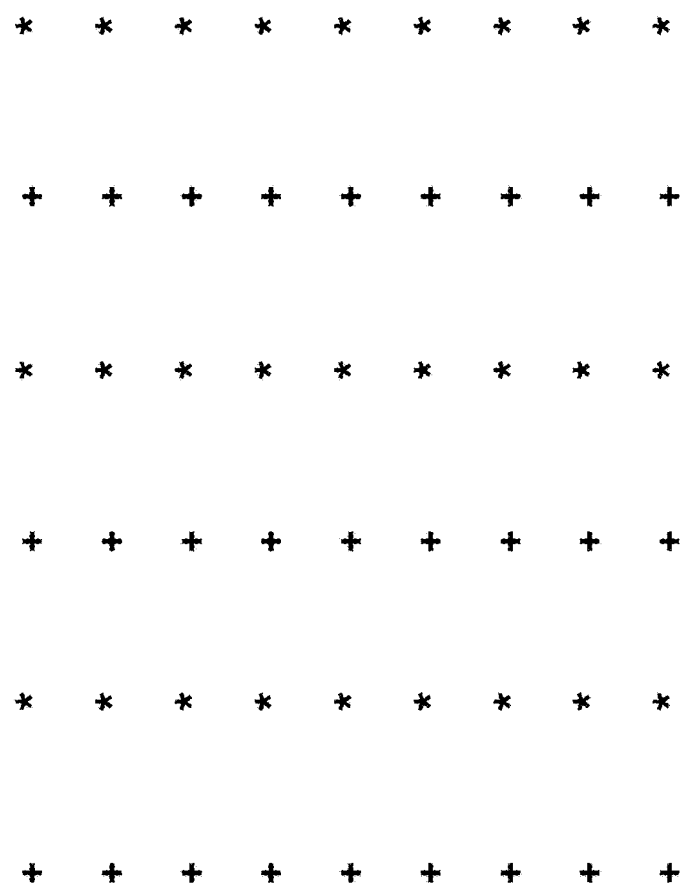

FIG. 6 schematically illustrates metal-ion-deposition islands on the scalp after rolling such a device over a user's scalp. In the schematic example of FIG. 6, cation metal-ion-deposition islands are represented as "+" (plus) while anion metal deposition islands are represented as "*" (star). In this example: (i) a distance between adjacent deposition islands of the same polarity (i.e. a distance between two neighboring pluses, or between two neighboring stars) is approximately equal to an inter-electrode distance for electrodes 102 disposed along a circumference of a disc; and (ii) a distance between deposition islands of opposite polarity (i.e., a distance between a neighboring star and plus) is approximately equal to a lateral distance between laterally-adjacent discs FIG. 6 relates to the situation of a 'single pass'—i.e. the roller is moved in a single linear direction over the scalp. In some embodiments, the roller may be moved 'back and forth' to perform a 'multi-pass' treatment. For example, the roller may be manually moved, the user may not move the roller in exactly a straight line introducing some degree of randomness in the distances between neighboring deposition-islands.

Figure 7:
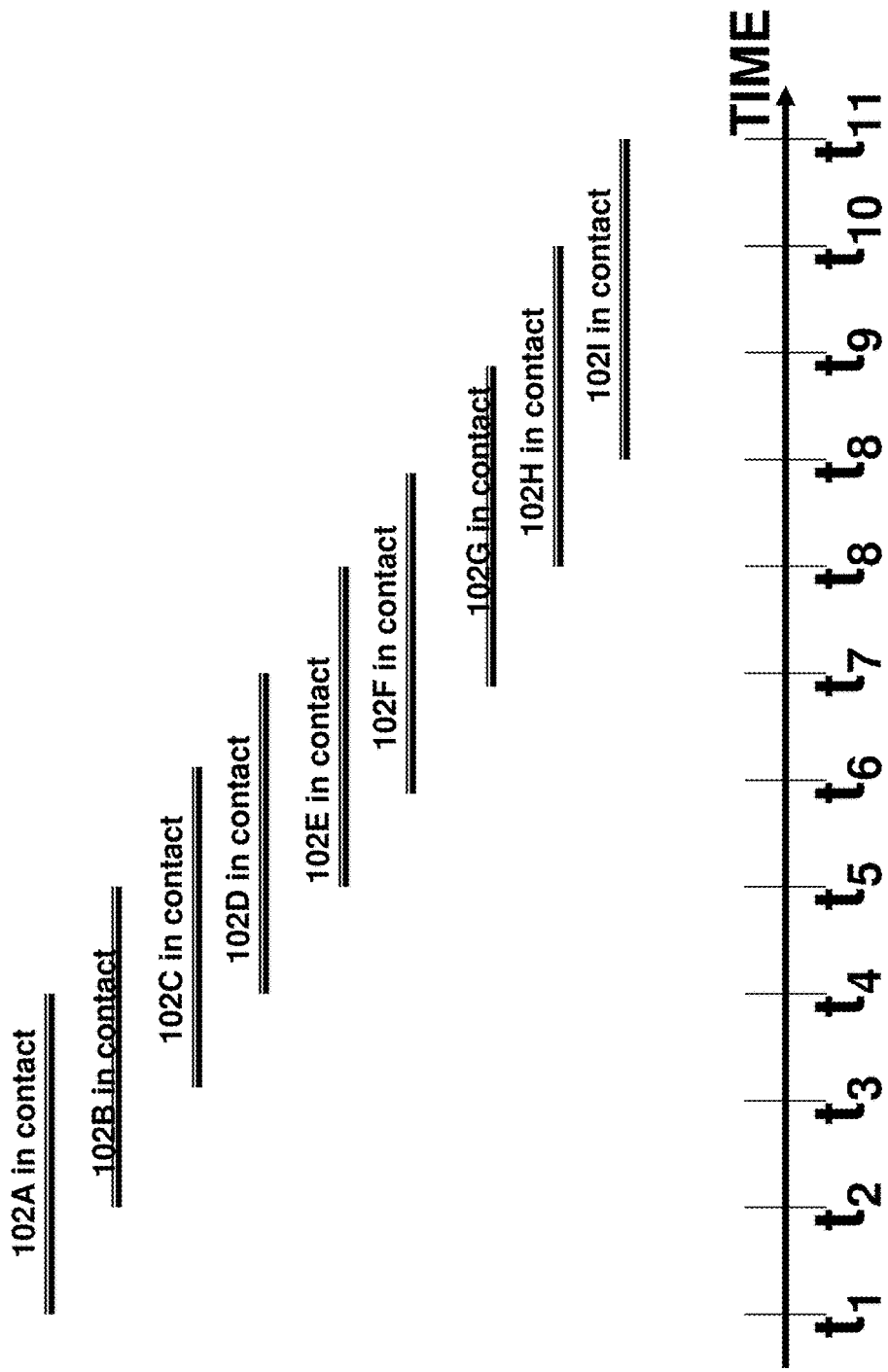
FIG. 7 illustrates a timeline showing where electrodes are brought into contact and out of contact with the scalp.

As illustrated in FIG. 5, in some embodiments, multiple electrodes of the same disc are simultaneously in contact with the scalp—in FIG. 5, electrodes 102H-102K are simultaneously in contact with the skin. FIG. 7 illustrates a timeline showing where electrodes 102A-102I are brought into contact and out of contact with the scalp—for example, electrode 102A is in contact with the scalp between times t1 and t4, electrode 102B is in contact with the scalp between times t2 and t5, and so-on.

When an electrode is in contact with the scalp, this is an 'electrode-scalp contact events'—FIG. 7 illustrates the commencement and conclusion of electrode-scalp contact events for electrodes 102A-102I in a heuristic example. Typically and as discussed below, each electrode-scalp contact event is quite brief—for example, at most 100 milli-seconds. Nevertheless, the present inventors have found that even this very brief contact is sufficient to form a small metal-deposition island on the scalp, and that it is useful to form a large number of distinct metal-deposition islands, preferably, within a relatively short period of time.

It is possible to employ external electrical power to increase a current between electrodes of opposite polarity through the scalp while both electrodes are in contact with the skin, rather than relying exclusively on the galvanic current between electrodes. In some embodiments, this may allow for a therapeutically significant quantity of metal ions in the metal-deposition-island formed by each contact event selected from a plurality of contact events, despite the relatively short electrode-scalp contact period of each contact event.

In some embodiments, some but not all contact events cause deposition of metal ions on the skin or scalp. In these embodiments, it is still possible to discuss a feature of a specific set of contact events where all events are the specific set are metal-ion-depositing—however, it is understood that additional contact events may be performed before and/or after and/or after a time-frame of the 'specific set of contact event.s'

Figure 8:
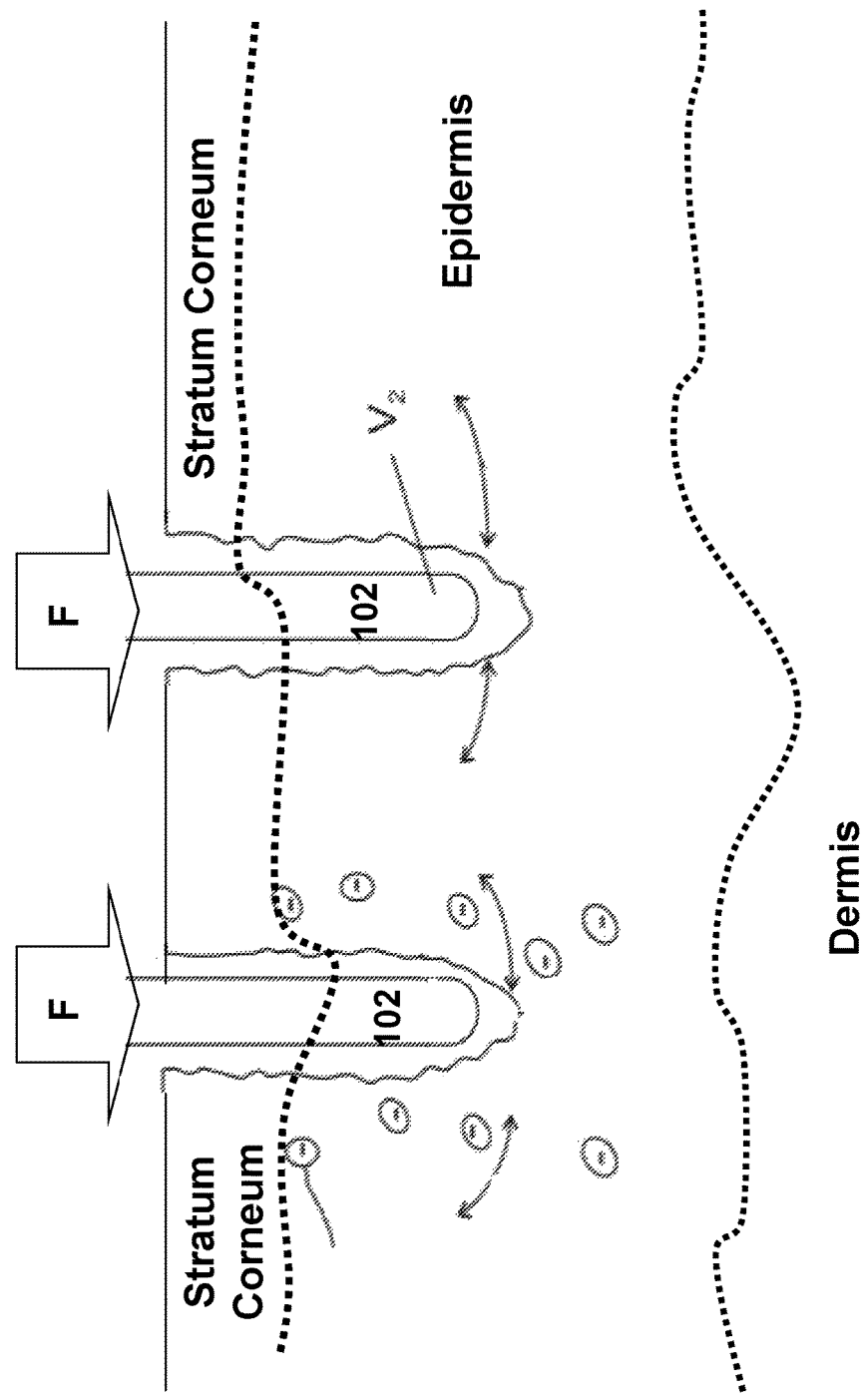
FIG. 8 illustrates a contact-event between electrodes and skin (e.g. of the scalp) wherein the electrodes do not penetrate into the dermis and ions are deposited on the skin (e.g. of the scalp).

In the example of FIG. 8, the electrodes 102 are 'non-wounding' since they do not enter the dermis. The rounded tips of the electrodes allows the user to provide significant pressure (e.g. at 0.5 mega-Pascal) to achieve a less invasive but sufficiently-stimulating 'micromassage' effect rather than a wounding or dermis-penetrating effect.

In the example of FIG. 8, negatively-charged ions are deposited on the skin to create the metal-ion-deposition island.

Figure 9:
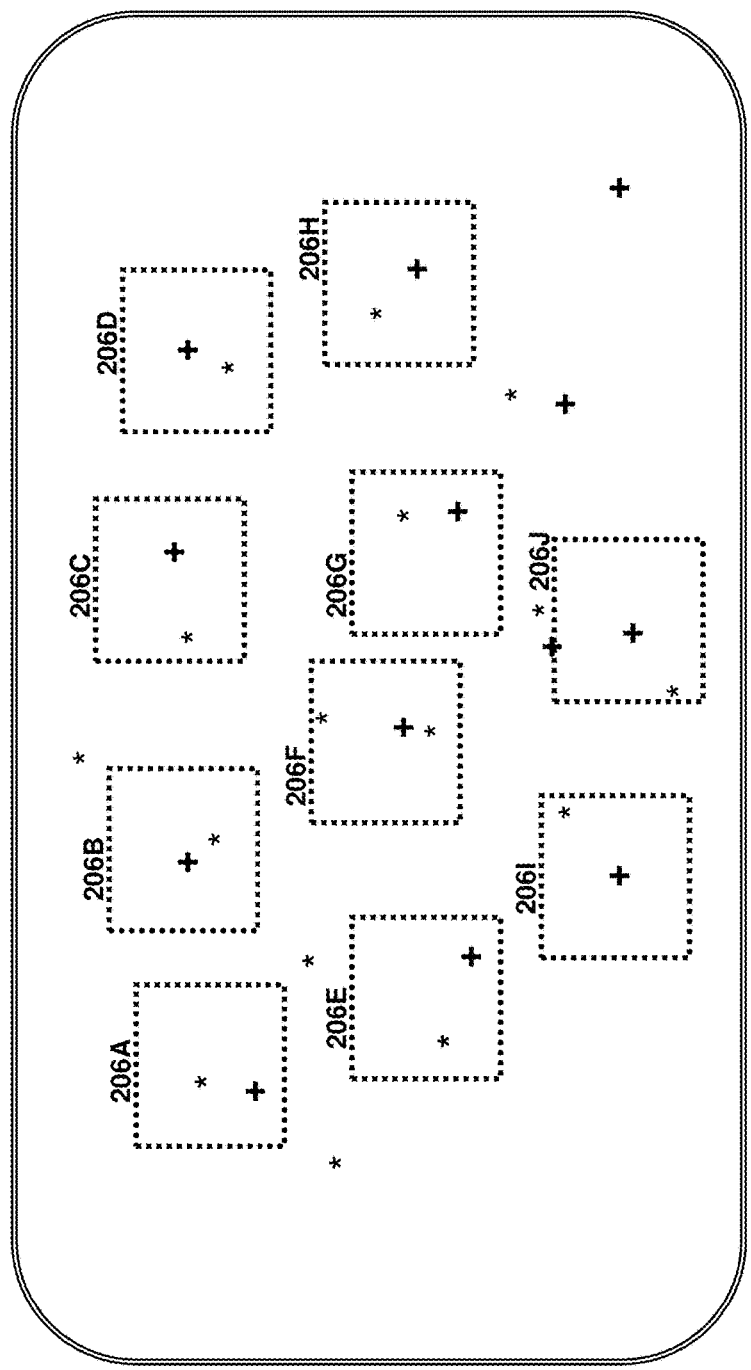

FIG. 6 illustrates on pattern of metal-ion-deposition islands. FIG. 9 illustrates another pattern. In the example of FIG. 9, a region of scalp comprises a plurality of different square 'patches' 206 (patches 206A-206J are illustrated) where a patch is a geometric construct to describe a portion of scalp. For example, a size of each scalp patch may be n mm×n mm where a n is a positive number having a value of at most 5. In the example of FIG. 9, cation and anion metal-deposition islands are both respectively applied to each patch of the ten patches.

Thus it may be said that at least one first-metal-deposition-island (i.e. represented by a '+') and at least one second-metal-deposition-island (i.e. represented by a '*') are both respectively and distinctly formed on each n mm×n mm scalp scalp-patch 206 selected from a 10-member scalp-patch sub-set of the scalp-patch set—for example, the 10 member scalp patch set {206A,206B,206C,206D,206E, 206F,206G,206H,206I,206J}.

The term 'metal-ion-deposition' island refers to deposition of metal on the user's scalp such that at the moment of deposition, the metal is deposited as an ion. There is no requirement for the metal to remain in ionic form thereafter. A metal-ion-deposition island forms a localized portion of metal on the user's scalp.

Examples described above relate to deposition by a multi-disc roller. Alternatively or instead of using disks, the electrodes may protrude from a single solid roller (e.g. spherical or cylindrical). In one example, electrodes are disposed at different longitudinal positions along the roller. As discussed below, the method may be performed using a non-roller device.

Also illustrated in FIG. 1 are axle 112, handle 114, housing 110, and power-source 116.

Although some electrode-scalp contact events form metal-deposition-islands, not every contact event is required to deposit metal on the user's scalp.

Example Performance Parameters

One non-limiting use case relates to the following parameters: (i) a disc radius of 16 mm and circumference of about 100 mm; (ii) about 100 protrusions per disc so that a distance between neighboring protrusions along a disk circumference is about 1 mm; (iii) the user applies pressure (e.g. at least 0.5 mega-Pascal or at least 1 mega-Pascal per electrode) has he/she rolls the disc array over his/her scalp, and thus rolls the disc area at a rate of about 0.3 revolutions/second corresponding to a linear velocity, assuming Assume a 2-disk device, the number of distinct contact events per second (i.e. where a protrusion is brought into and out-of contact with the scalp) in this example is about 0.3*100*2≈65 contact-events per second. In this situation, assuming the user continuously rolls the disc over his/her scalp for at least one minute, the scalp would be subjected to about 4000 electrode-scalp contact events per minute.

Assuming an 8-disk device, the user's scalp would be subjected to about 16,000 contact events per minute.

Cross sectional area of individual electrode-scalp contact-location and/or metal-deposition island: In an exemplary embodiment of the invention, the cross sectional area of an electrode-scalp contact location is selected to be, for example, about 1 mm$^2$, about 0.1 mm$^2$, about 0.01 mm$^2$, about 0.001 mm$^2$, about 0.0001 mm$^2$, or other smaller, intermediate or larger sizes are used.

Density: In an exemplary embodiment of the invention, the density of contact locations and/or deposition islands per unit area of scalp to be treated is selected, for example, about 1 locations/mm$^2$, about 5 locatinos/mm$^2$, about 8, locations/mm$^2$ about 10 locatinos/mm$^2$, or other smaller, intermediate or larger densities are used.

Total electrode-scalp contact area per electrode per contact event: In an exemplary embodiment of the invention, the area of scalp to be subjected to ion-deposition from the total area of the scalp to be treated is selected. The 'fill factor' is selected to be, for example, about 10%, about 1%, about 0.1%, about 0.01% of the area to be treated, or other smaller, intermediate or larger values are used. In one non-limiting example, the fill factor is (i) at least 5% or at least about 7.5% and/or (ii) at most 50% or at most 40% or at most 30% or at most 20% or at most 15%.

Figure 10A:
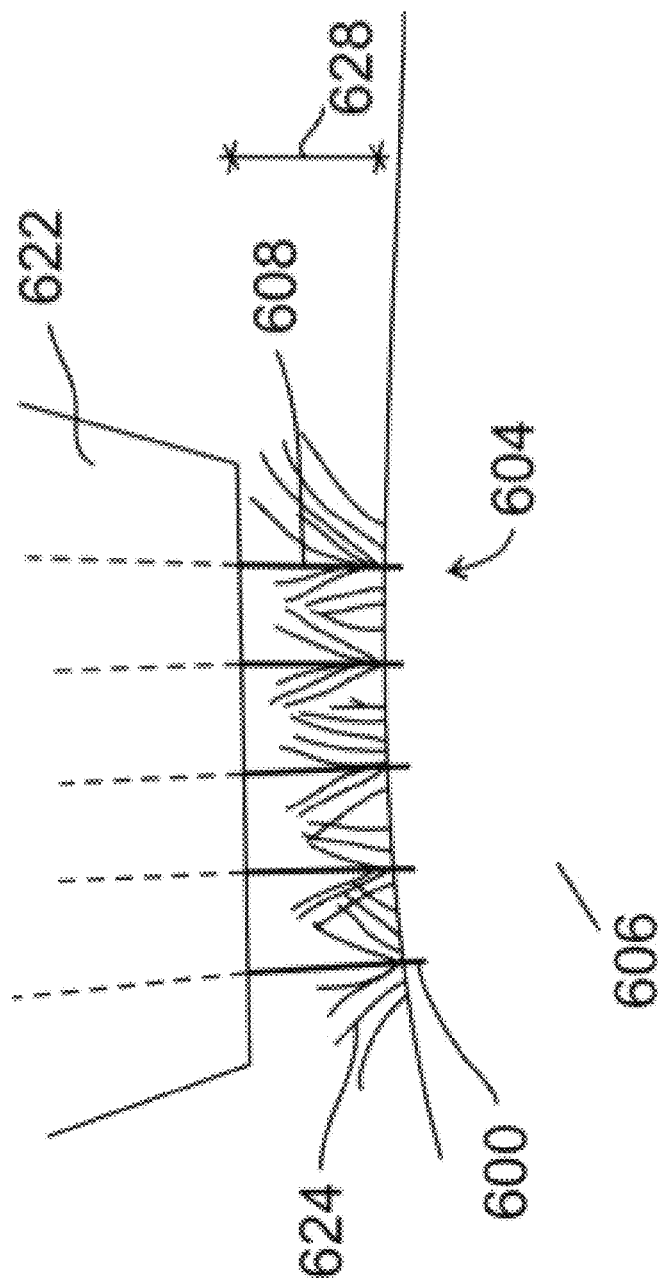
FIG. 10A-10B are sides view of an electrode array causing a pattern of deposition islands.
Figure 10B:
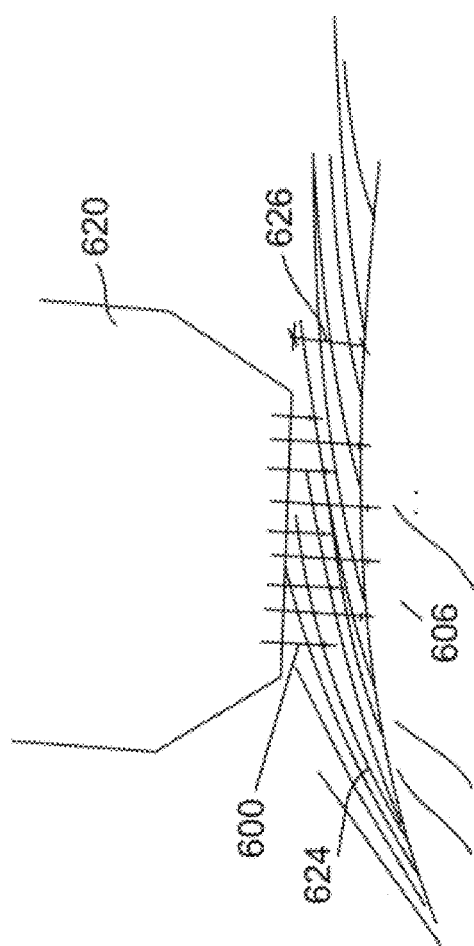

Gaps between deposition islands: In an exemplary embodiment of the invention, the distance between deposition-islands is selected. Optionally, the space between deposition-islands along a first axis is selected. Optionally or additionally, the space between deposition-islands along a second axis is selected, for example, the first and second axes are perpendicular to one another. In some embodiments, gaps along at least one axis are selected according to the existing amount of hair at the area to be treated, for example, relatively larger spaces are selected for a region with relative denser hair and/or hair having a relatively larger diameter. Existing hair may be displaced to the gaps between the deposition-islands. Spaces between deposition islands along the first axis are selected to be about, for example, 3 mm, about 4.5 mm, about 6 mm, or other smaller, intermediate or larger spaces are used. Spaces between electrode deposition islands along the second axis are selected to be, for example, about 0.3 mm, about 0.5 mm, about 1 mm, about 1.5 mm, about 2 mm, or other smaller, intermediate or larger values are used FIG. 10A-10B are sides view of a electrode array 604 using electrodes 600 to cause a pattern of deposition islands in the scalp 606.

In an exemplary embodiment, an actuator moves the electrode up and/or down.

In some embodiments, a group of electrodes is attached to a single actuator.

In an exemplary embodiment of the invention, a distance 626 and/or 628 between scalp 606 and device head 620 and/or 622 is set to provide a volume for hair 624 during penetration of electrodes 600 into scalp 606. Hair 624 can be displaced into the volume to let electrodes 600 contact scalp 606 to allow the full length of electrodes 600 to enter. Distance 628 can be set for example, by diameter of discs 608 and/or by selecting the central hinge position within device head 620.

In an exemplary embodiment of the invention, the pattern of deposition-islands is parallel straight lines, for example, for a roll of discs 608. Optionally, complex and/or random patterns of deposition islands can be created by repeated rolling of discs 608 over the scalp. Optionally, one or more discs each comprise multiple electrodes, arranged, for example, in a circumferential arrangement and/or along the thickness of the wheel, on the surface contacting the skin.

In an exemplary embodiment of the invention, electrodes 600 are made out of a biocompatible material, non-limiting examples include; metals (e.g., steel, silver, gold), alloys, glass, plastic, ceramic.

In an exemplary embodiment of the invention, electrodes 600 are coated with a type I 5a-reductase inhibitor, for example the metals zinc and/or copper.

Electrode/Protrusion Actuators

FIGS. 11A-11F are illustrations of embodiments of electrode actuators, in accordance with some embodiments of the invention. Optionally, electrode actuators act as vibrational elements, to vibrate electrodes according to the selected vibrational protocol.

In some embodiments of the inventions, one or more non-limiting examples of actuators include; piezoelectric elements, motorized linear actuators, and/or shape memory alloy actuators.

In some embodiments of the invention, electrodes are individually vibrated. Alternatively or additionally, groups of electrodes are vibrated together. Optionally, vibration is performed by an off-axis spinning mass, for example, the direction of the axis determines the plane of vibration. For example, translating the movement to a linear direction, pushing on a piston mass creates a linear vibration.

FIG. 11A is an isometric view, and FIG. 11B is a cross sectional view of a electrode array 702, for example described with reference to FIG. 10B. Each electrode 700 (of array 702 is coupled to an actuator 704. Optionally, each electrode 700 is coupled to a separate actuator 704. Optionally, actuators 704 are attached to a power control 705.

For example, the actuators 704 may be controlled to maintain the electrode in contact with the scalp for only brief electrode-scalp contact events.

FIG. 11C is an isometric view, and FIG. 11D is a cross sectional view of a electrode array 706. Two or more electrodes are controlled by actuators, for example, array of nine electrodes 708 is controlled by actuator 710 and, for example, array of electrodes 706 is controlled by actuator 711. There are two or more groups of electrodes, for example, four groups 708, 730, 732 and 734 of nine electrodes in each group are controlled by four actuators 710, 736, 738 and 740.

Figure 11F:
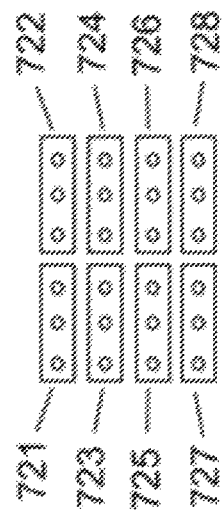
Figure 11E:
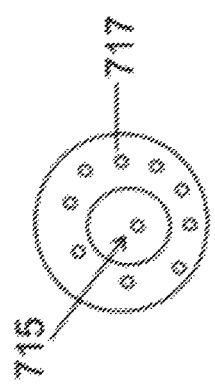

Electrode groups can be arranged in a variety of patterns. Non-limiting examples include the checkerboard pattern as illustrated in FIG. 11D, a bull's eye pattern as illustrated in FIG. 11E and/or a side by side tile pattern as illustrated in FIG. 11F. For example, the bull's eye pattern (FIG. 11E) may comprise one electrode 715 in an inner circle and at least two electrodes in electrode array 717 in an outer circle and, for example, the side by side tile pattern (FIG. 11F) may comprise eight groups 721, 722, 723, 724, 725, 726, 727 and 728 of electrodes.

In some embodiments, at least two groups (FIG. 11F) may touch the scalp simultaneously. For example, the device is configured so that several actuators receive a signal to "lower" and touch and/or penetrate the scalp simultaneously. Optionally or alternatively, several electrodes are connected to a single actuator 710 and go up and down together. Optionally, the electrodes conform (or are advanced to conform) to the scalp curvature and penetrate together. In some embodiments, the electrodes are equipped with a spring to facilitate conformity to the scalp curvature.

In an exemplary embodiment, 721 and 722 may touch the scalp simultaneously, 722 and 723 may touch the scalp simultaneously, or 723 and 724 may touch the scalp simultaneously, or 724 and 725 may touch the scalp simultaneously, or 725 and 726 may touch the scalp simultaneously, or 721, 722 and 728 may touch the scalp simultaneously, or 722, 725 and 727 may touch the scalp simultaneously or another combination of groups may touch the scalp simultaneously. Optionally, more than two types of ions are discharged from the electrodes. FIG. 7G is an isometric view of a single injector.

Figure 11I:
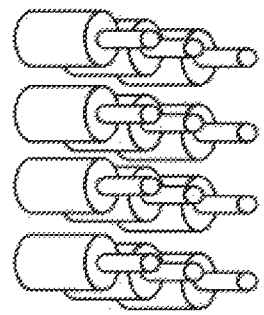
Figure 11H:
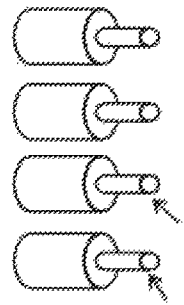
Figure 11G:
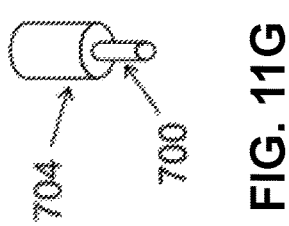

FIG. 11H is an isometric view of a 1-dimensional array of electrodes. FIG. 11I is an isometric view of a 2-dimensional array of electrodes.

Reference is now made to FIGS. 12A-12D. In some embodiments, the number of ions deposited during treatment is controlled by adapting the voltage (see, for example, the methods described in Chizmadzhev et al, *Electrical Properties of Skin at Moderate Voltages: Contribution of Appendageal Macropores*), by adapting the temperature (see, for example, the methods described in Maulsby et al, *The interrelationship between the galvanic skin response, basal resistance, and temperature*), and/or by adapting the frequency. Increasing the voltage, temperature and frequency can each increase the number of ions deposited. For example, the number of ions deposited during treatment is controlled in an open loop manner by determining the voltage before beginning treatment. Alternatively, the number of ions deposited during treatment is controlled in a closed loop manner by determining the voltage during the treatment based on feedback received from sensors incorporated into the device.

In some embodiments, controlling the ions deposited is done directly by measuring the charge of each polarity (ion type) or of both, for example, by measuring and integrating the (absolute) current passed through each type of disk set or through both. The existence of current indicates the unit is in actual use. A degradation of current indicates a faulty unit, improper contact, or other means. Excessive current might indicate a faulty unit, or excessive moisture on the scalp (and therefore not enough current through the scalp).

In some embodiments, the mass of metal ions discharged from the electrodes may be calculated by a formula. For example, assuming the charge C is ionic, and the oxidation state Z, the mass m of metal ions discharged from the electrodes (w is the atomic mass, e the electron's charge, Na is Avogadro's number) is computed as follows:

$$m = \frac{C \cdot w}{e \cdot Z \cdot N_a}$$

In some embodiments, ion injecting electrodes that touch the scalp are connected to one terminal of a power source and an electrode that does not touch the scalp is connected to a second terminal of the power source. For example, the electrode that does not touch the scalp may be connected to a part of the body other than the scalp. For example, the device may comprise a handle comprising an electrode designed to touch the palm of a person holding the handle.

In some embodiments, the efficiency of the deposition of ions is enhanced, for all users or for a specific user, by performing a "calibration phase" in which the same region is treated for a period of a time while changing each parameter slightly and measuring the real-time response in current. Optionally, different treatment parameters may be chosen for different scalp areas of same user. Optionally, different treatment parameters may be chosen for different users.

In some embodiments, the efficiency of the deposition of ions is enhanced through general improvements in the parameters, for example, preparing a better cross section of the electrodes and/or starting with more efficient voltage and frequency. Optionally, the efficiency of the deposition of ions is enhanced through dynamic modification of changeable treatment parameters through closed-loop feedback/control.

In some embodiments, ion penetration increases blood flow when the electrical fields generated by the small charge deposits create a MENS (microcurrent electrical neuromuscular stimulation) effect in the skin. Optionally, the MENS effect shortens skin healing times. Optionally, the electrical fields invigorate movement of essential ions and stimulate the skin systems into an increased rate of activity.

FIG. 12A is an illustration of an array of electrodes 802 depositing materials 804 beneath the skin 806 surface of scalp, in accordance with an exemplary embodiment of the invention. For simplicity purposes, array 802 comprises four electrodes 808, having the material 804 to deposit located at the part of the electrode 808 that contacts scalp 806.

In an exemplary embodiment of the invention, electrodes 808 are made of material 804. Alternatively, electrodes 808 are coated with material 804. Optionally or alternatively, 830, 832, 834 and/or 836 represent electrical potentials which may exist on electrodes 808.

In an exemplary embodiment of the invention, two different electrodes 808 to be electrically coupled have two different materials 804 at their ends. For example, alternating discs (e.g., as illustrated in FIG. 1) are made from different materials, for example, copper and zinc.

In some embodiments, scalp 806 acts as a bridge, placing two electrodes having dissimilar metals in electrical contact. The metals can undergo galvanic corrosion, where one metal dissolves in scalp 806, while the other metal absorbs ions from scalp 806. For example, if one metal is zinc and the other metal is copper, the zinc will dissolve and the copper will accumulate. Optionally, material 804 is chosen to have other depositing effects. Optionally or additionally, current is forced in the opposite direction.

FIG. 12B is an illustration of ion deposition into scalp 806 for example using a galvanic cell set-up, in accordance with an exemplary embodiment of the invention. Optionally, a power source 812 electrically couples a first electrode 814 and a electrode electrode 816. For example, each electrode 814 and 816 may be coated electrodes comprising different materials at the ends 815 and 817, for example, electrode 814 touches scalp 806 at end 815 with zinc and electrode 816 at end 817 with copper. Optionally, power source 812 emits Alternating Current (AC). Optionally, power source 812 emits Direct Current (DC).

Figure 12D:
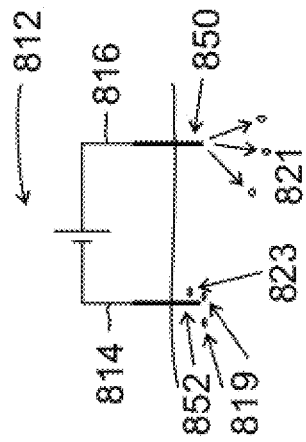
Figure 12C:
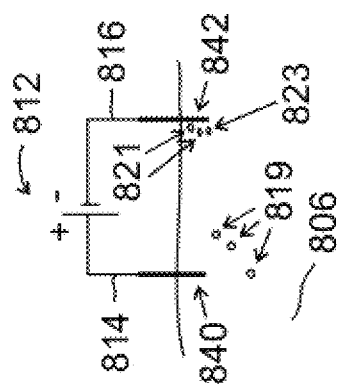

FIG. 12C is an illustration of using the set-up as in FIG. 12B to release zinc ions into scalp 806, in accordance with an exemplary embodiment of the invention. The positive pole of power source 812 is electrically connected to electrode 814 with zinc (e.g., acting as the anode 840), and the negative pole is electrically connected to electrode 816 with copper (e.g., acting as the cathode 842) Zinc ions 819 are discharged from electrode 814 into scalp 806, and copper ions 821 and/or other ions 823 are accumulated from scalp 806 onto electrode 816.

In an exemplary embodiment of the invention, the voltage of power source 812 as in FIG. 12C is, for example, about 1V, about 3V, about 5V, about 7V, about 10V, about 30V, or other smaller, intermediate or larger values are used.

FIG. 12D is an illustration of using the set-up of FIG. 12B to release copper ions into scalp 806, in accordance with an exemplary embodiment of the invention. The positive pole of power source 812 is electrically connected to electrode 816 with copper (e.g., acting as the anode 850), and the negative pole is electrically connected to electrode 814 with zinc (e.g., acting as the cathode 852). Copper ions 821 are discharged from electrode 816 into scalp 806, and zinc ions 819 and/or other ions 823 are accumulated from scalp 806 onto electrode 814.

In an exemplary embodiment of the invention, the voltage of power source 812 as in FIG. 21D is at least greater than the standard potential for the reaction, for example, above 1.10 Volt.

In an exemplary embodiment of the invention, power source 812 is an alternating current source. The frequency of source 812 can be selected to result in a desired ion deposition pattern, for example alternating between the set-ups as described in FIGS. 12C and 12D. For example, the frequency of source 812 is selected to be substantially half of the rate of electrode-scalp contact events per second, for example when using the hair stimulation device with rolling discs, for example, as described with reference to FIG. 1. For example, if the device is rolled over the scalp to achieve a rate of scalp-electrode contact events of 30 events per second and the frequency of source 812 is 15 Hz, the ions deposited during each electrode-contact will alternate, for example between copper and zinc. Furthermore, different ions will be deposited at different locations.

In some embodiments of the invention, the AC waveform (e.g., duty cycle) is selected according to the ratio of the desired material deposition. For example, to achieve a 10:1 ratio (e.g., of zinc:copper), a waveform having a 10:1 ratio (91% duty cycle) is selected. Alternatively or additionally, the number of electrodes coated with each material is selected according to the desired deposition ratio, for example, the number of electrodes coated with zinc relative to the number of electrodes coated with copper is 10:1.

In some embodiments of the invention, power source 812 is a direct current source. The polarity of source 812 can be selected to result in a desired ion type and/or deposition pattern. For example, according to the set-ups of FIGS. 12C and/or 12D. The set-up of FIG. 12C can also be achieved without source 812, for example by electrically connecting electrodes 814 and 816.

In some embodiments of the invention, materials (e.g., ions) are added directly to the scalp, for example in the form of a lotion, gel and/or water. Non-limiting examples of ions in this form include $ZnSO_4$, $CuSO_4$. The lotion can be added in addition to the use of coated electrodes, or instead of coated electrodes (e.g., using uncoated electrodes). Optionally, the ions penetrate below the surface of the skin.

Electrical Stimulation

In an exemplary embodiment of the invention, the scalp is stimulated by applying one or more currents and/or voltages to areas of the skin, for example, an electrical stimulation protocol is selected. Optionally, a plurality of currents and/or voltages are applied to the scalp, for example different voltages and/or currents to different areas and/or between different electrodes.

In an exemplary embodiment of the invention, the electrical stimulation is separate from the current applied to the electrodes to release ions, for example, Optionally, electrical stimulation is applied by one or more discs and/or electrodes, and ion deposition is applied by different discs and/or electrodes. Optionally, the electrodes to apply electrical stimulation but not ion deposition are inert, for example, made from platinum. Alternatively, a voltage is applied to the electrodes to prevent ion deposition by the galvanic effect. Alternatively or additionally, electrical stimulation and ion deposition overlap, for example, applied by the same discs and/or electrodes.

Inventors hypothesize that selectively applying a plurality of electrical stimulation patterns (e.g., voltages and/or currents) to the scalp will promote hair growth. However, the efficacy of some embodiments of the invention can be unrelated to the underlying theory, and work even if the theory is incorrect.

In an exemplary embodiment of the invention, the electrical stimulation protocol comprises one or more variables. Non-limiting examples of selectable parameters include:

Geometric voltage and/or current distribution pattern: The pattern of applied voltages and/or current per electrode. For example, the voltage and/or current at each electrode is independently controlled and/or groups of electrodes have similar voltages and/or current (e.g., alternating electrodes have similar voltages and/or currents, electrodes having the same type of material (for example zinc or copper) have similar voltages and/or currents).

In some embodiments of the invention, the voltage and/or current pattern is substantially the same, for example, the same electrode is associated with the same charge and/or current. Alternatively or additionally, the voltage and/or current pattern is dynamic, for example dynamic throughout the array, and/or a region of the array. For example, in a relatively large array, a relatively small patch of the electrical pattern can be scanned across the array.

A potential advantage of two groups of electrodes with different voltages is the controlled patterning of current and/or ion deposition. For example, local stimulation may be superior to global. Potentially, division to several groups allows greater flexibility and/or controllability of the current. For example, current can be applied (e.g., to different groups, at different intensities) simultaneously or in a time-divided manner.

Voltage and/or current distribution pattern over time: The pattern of applied voltage and/or current per electrode can vary over time. For example, an alternating current and/or voltage can be applied to vary the voltage and/or current between two or more electrodes (or groups of electrodes). In the case of using the device with discs for example in FIG. 1 (e.g., rolling the discs with electrodes on the scalp), selecting an alternating frequency that is less than the frequency of rotation can result in increasing the diversity and/or gradients of voltages and/or currents applied underneath the skin surface. Inventors hypothesize that applying various patterns of voltage and currents to the skin stimulates hair growth. Potentially, applying varying time and/or location stimulations improves stimulation of local points, for example hair follicles Direct current (DC) offset: A voltage offset can be applied to the pattern applied to one or more electrodes. In an exemplary embodiment of the invention, the DC offset is calibrated, for example, from −3 volts to +3 volts, or other smaller, intermediate or larger values are used. In an exemplary embodiment of the invention, the DC disc to disc relative voltage ranges, for example, from 0 to 30 volt, or other smaller, intermediate or larger values are used.

Alternating current (AC) peak to peak voltage: In an exemplary embodiment of the invention, the peak to peak voltage of the AC varies, for example, from −10 volts to +10 volts, or other smaller, intermediate or larger values are used.

Frequency of AC: In an exemplary embodiment of the invention, the frequency of AC ranges, for example, from 10-1000 Hz, or other smaller intermediate or larger values are used.

Waveform of AC: In an exemplary of the invention, the waveform of AC is rectangular. Alternatively, other waveforms are used, non-limiting examples include sinusoidal, triangular, sawtooth.

Maximal Current: In an exemplary embodiment of the invention, the total electrical current is less, for example, than 0.5, less than 1, less than 2 milliAmperes, or other smaller, intermediate or larger values are used.

Various embodiments and aspects of the present invention as delineated hereinabove and/or as claimed in the claims section below find experimental support in the following examples:

EXAMPLE

Experiment

Reference is now made to the following example, which together with the above descriptions illustrates some embodiments of the invention in a non-limiting fashion. In particular, features described below may be used without other described features and in conjunction with methods and/or apparatus as described above.

Material and methods—An experiment over 2-4 months was conducted on 26 volunteers all of whom were suffering from baldness. Each volunteer was provided with a roller-like device (see, for example, FIG. 1) configured to form both zinc-ion-deposition islands and copper-ion-deposition islands when rolled over the scalp. As the user rolled the device over his respective scalp, electrodes of the roller device were each briefly brought into contact with and out of contact with the scalp. The device used included 8 disks with non-puncturing electrode protrusions, used for several minutes at least twice a week by users.

Each disk had about 100 protrusions, about 0.2 mm wide and a triangular protrusion with effective contact length of 1 mm (tip is about 0.1 mm)

Disks were alternatively coated with Zinc and Copper.

Electrical current applied was about 30V at 40 Hz.

No LLLT was applied.

For each subject, it was possible, per treatment site, to monitor a number of features related to hair density at the treatment site, such as the overall hair density, terminal hair-density and non-terminal hair density. Results are summarized in FIGS. 13A-13B. The skilled artisan who reviews FIGS. 13A-13B will appreciate that the device and method appeared to play a significant roll in reversing hair-loss.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is expected that during the life of a patent maturing from this application many relevant hair stimulation devices will be developed and the scope of the term hair stimulation device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of treating or preventing a hair-condition of a user, the user's scalp dividable into a scalp-patch-set of n mm ×n mm non-overlapping square scalp patches, n being a positive number having a value of at most 5, the method comprising:
    subjecting the user's scalp to at least q distinct electrode-scalp contact events within a time-interval of at most one minute, the time interval being dividable into m non-overlapping equal-duration sub-intervals covering the time-interval, m being a positive integer having a value of at least 5, q being a positive integer having a value of at least 200, the method performed such that:
    i. for at least a majority of the electrode-scalp contact events, no electrode of the event enters into the dermis;
    ii. a duration of each electrode-scalp contact event is at most 100 milliseconds;
    iii. an electrode-scalp contact area for each electrode-scalp contact event is at most 10 mm$^2$;
    iv. for each electrode-scalp contact event, an electrical current flows between the electrode and the scalp so as to deposit electrode-released ions of a first metal or of a second metal on the scalp, thereby forming a respective metal-ion-deposition island on the user's scalp;
    v. for each of the m non-overlapping equal-duration sub-intervals, at least p electrode-scalp contact events occur, p being a positive integer having a value of at least 1;
    vi. at least 5% of the electrode-scalp contact events are first-metal-depositing and at least 5% of the electrode-scalp contact events are second-metal-depositing; and
    vii. at least one first-metal-deposition-island and at least one second-metal-deposition-island are both respectively and distinctly formed on each n mm ×n mm scalp scalp-patch selected from a 10-member scalp-patch sub-set of the scalp-patch set.

2. The method of claim 1 wherein during at least some of the electrode-scalp contact events, externally-generated electrical current is respectively forced between the electrode and the scalp so as to respectively deposit or increase a deposition-rate of electrode-released ions of the first or second metal onto the scalp.

3. The method of claim 1 wherein a value of q is at least 1000.

4. The method of claim 1 wherein a value of p is at least 5.

5. The method of claim 1 wherein a value of m is at least 10.

6. The method of claim 5 wherein a value of p is at least 5.

7. The method of claim 1 wherein for at least 75% of the electrode-scalp contact events, no electrode enters into the dermis.

8. The method of claim 1 wherein at least 20% of the events are first-metal-depositing.

9. The method of claim 8 wherein at least 20% of the events are second-metal-depositing.

10. The method of claim 1 performed so that at least four metal-deposition-islands are respectively and distinctly formed on each n mm ×n mm scalp-patch selected from a 10-member scalp-patch sub-set of the scalp-patch set, the four metal-deposition islands comprising at least two first-metal-depositing islands and at least two second-metal-depositing-islands.

11. The method of claim 1 wherein a duration of each electrode contact event is at most 50 milliseconds.

12. The method of claim 1 wherein a duration of each electrode contact event is at most 25 milliseconds.

13. The method of claim 1 wherein an electrode-scalp contact area for each electrode-scalp contact event is at most 5mm$^2$.

14. The method of claim 1 wherein during each of a majority of the electrode-scalp contact events, the scalp is respectively subjected to an electrode-applied pressure of at least 0.5 mega-Pascals.

15. The method of claim 1 wherein during each of at least 75% of the electrode-scalp contact events, the scalp is respectively subjected to an electrode-applied pressure of at least 0.5 mega-Pascals.

16. The method of claim 1 wherein during each of a majority of the electrode-scalp contact events, the scalp is respectively subjected to an electrode-applied pressure of at least 1 mega-Pascal.

17. The method of claim 1 wherein during each of at least 75% of the electrode-scalp contact events, the scalp is respectively subjected to an electrode-applied pressure of at least 1 mega-Pascal.

18. The method of claim 1 wherein a value of q is at least 250, and wherein for each of the electrode-scalp contact events, at least some of the released metal-ions deposited on the scalp are provided from an electrode interior of the electrode and/or from an electrode metal-coating that is integrally formed with the electrode.

19. The method of claim 1 wherein during a majority of the electrode-scalp contact events, externally-generated electrical current is forced between the electrode and the scalp so as to deposit or increase a deposition-rate of electrode-released ions of the first or second metal onto the scalp.

20. The method of claim 1 wherein each electrode-scalp contact event is performed by an electrode having a rounded tip.

21. The method of claim 1 wherein each electrode-scalp contact event is performed by an electrode that is at least partially constructed from the first or second metal.

22. The method of claim 1 wherein each electrode-scalp contact event is performed by an electrode having disposed therein a reservoir of the first or second metal.

23. The method of claim 1 wherein each electrode-scalp contact event is performed by an electrode that is coated with the first or second metal.

24. The method of claim 1 wherein: (i) the method is performed by a device comprising a roller having a disposed thereon a plurality of electrode-protrusions; and (ii) rotational motion of the roller drives the electrode-scalp contact events.

25. The method of claim 1 wherein (i) the method is performed by a device comprising a motor and one more electrodes mechanically coupled to the motor, (ii) operation of the motor causes motion of the one or more electrodes, to drive the electrode-scalp contact events.

* * * * *